United States Patent
Chandler et al.

(10) Patent No.: US 6,506,584 B1
(45) Date of Patent: Jan. 14, 2003

(54) APPARATUS AND METHOD FOR ULTRASONIC TREATMENT OF A LIQUID

(75) Inventors: Darrell P. Chandler, Richland, WA (US); Gerald J. Posakony, Richland, WA (US); Leonard J. Bond, Richland, WA (US); Cynthia J. Bruckner-Lea, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/561,832

(22) Filed: Apr. 28, 2000

(51) Int. Cl.$^7$ ............................................. C12N 13/00
(52) U.S. Cl. ................................................. 435/173.7
(58) Field of Search ...................................... 435/173.7

(56) References Cited

U.S. PATENT DOCUMENTS

| | | | |
|---|---|---|---|
| 3,715,104 A | | 2/1973 | Cottell |
| 3,865,350 A | * | 2/1975 | Burtis |
| 4,205,966 A | | 6/1980 | Horikawa ................. 55/15 |
| 4,492,338 A | | 1/1985 | Marelli ..................... 239/102 |
| 4,764,021 A | * | 8/1988 | Eppes |
| 5,026,167 A | * | 6/1991 | Berliner, III |
| 5,032,027 A | * | 7/1991 | Berliner, III |
| 5,482,726 A | * | 1/1996 | Robinson, Jr. |
| 5,538,628 A | | 7/1996 | Logan ....................... 210/198.1 |
| 5,629,185 A | * | 5/1997 | Stanzl et al. |
| 5,979,664 A | | 11/1999 | Brodeur .................... 209/155 |
| 6,244,738 B1 | * | 6/2001 | Yasuda et al. |

FOREIGN PATENT DOCUMENTS

| | | | | |
|---|---|---|---|---|
| CA | 2151874 | | 12/1996 | |
| DE | 4241154 C1 | * | 3/1994 | |
| DE | 4407564 A1 | * | 9/1995 | ............. C02F/1/72 |
| DE | 19820466 A1 | * | 11/1999 | ............. B06B/1/06 |
| FR | 2708873 A1 | * | 2/1995 | ........... B01D/11/02 |
| GB | 1 407 842 | | 9/1975 | |
| JP | 10-29716 | | 2/1998 | |

OTHER PUBLICATIONS

Belgrader, et al., *A Minisonicator to Rapidly Disrupt Bacterial Spores for DNA Analysis*, Anal. Chem., 1999, 71, pp. 4232–4236.

Mcintosh, et al., *Continuous Treatment of Micro Organisms by High Intensity Ultrasound*, Oct. 20–21, 1970, pp. 6–8.

T.J. Mason, *Industrial Sonochemistry: Potential and Practicality*, Ultrasonics, 1992, vol. 30, No. 3, pp. 192–196.

* cited by examiner

Primary Examiner—Jon P. Weber
(74) Attorney, Agent, or Firm—Stephen R. May

(57) ABSTRACT

The present invention is an apparatus and method for ultrasonically treating a liquid to generate a product. The apparatus is capable of treating a continuously-flowing, or intermittently-flowing, liquid along a line segment coincident with the flow path of the liquid. The apparatus has one or more ultrasonic transducers positioned asymmetrically about the line segment. The ultrasonic field encompasses the line segment and the ultrasonic energy may be concentrated along the line segment. Lysing treatments have been successfully achieved with efficiencies of greater than 99% using ultrasound at MHz frequencies without erosion or heating problems and without the need for chemical or mechanical pretreatment, or contrast agents. The present invention overcomes drawbacks of current ultrasonic treatments beyond lysing and opens up new sonochemical and sonophysical processing opportunities.

15 Claims, 5 Drawing Sheets

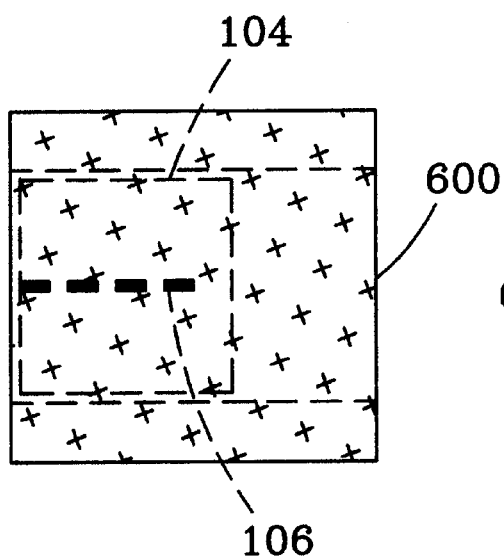
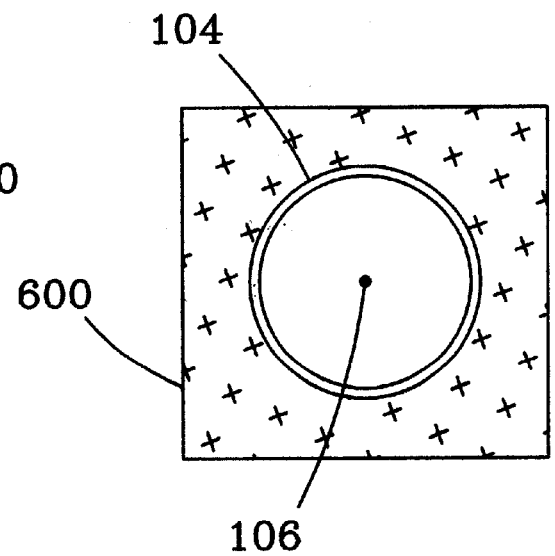
*Fig. 5a*  *Fig. 5b*
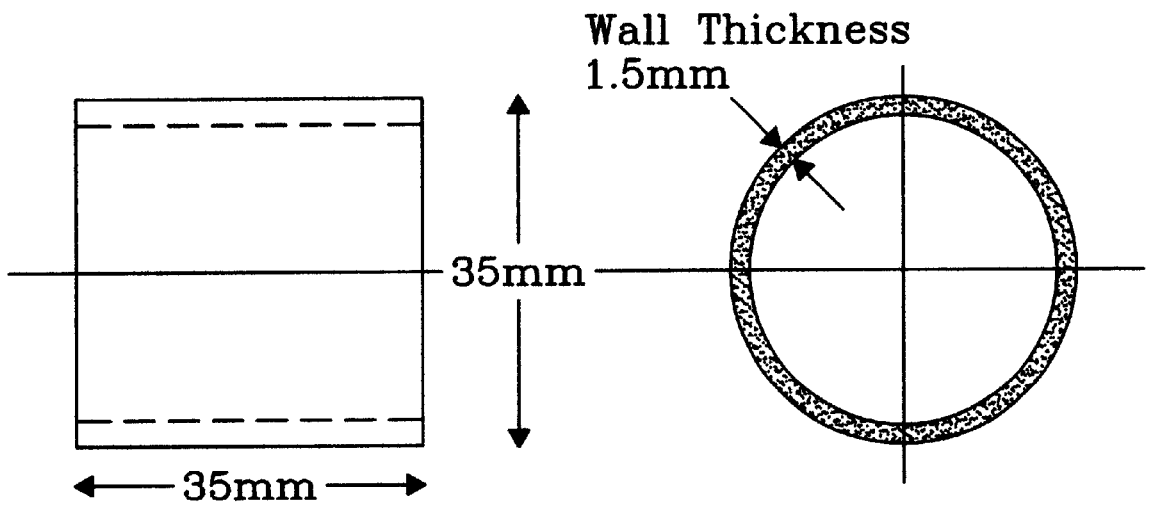
*Fig. 6a*  *Fig. 6b*

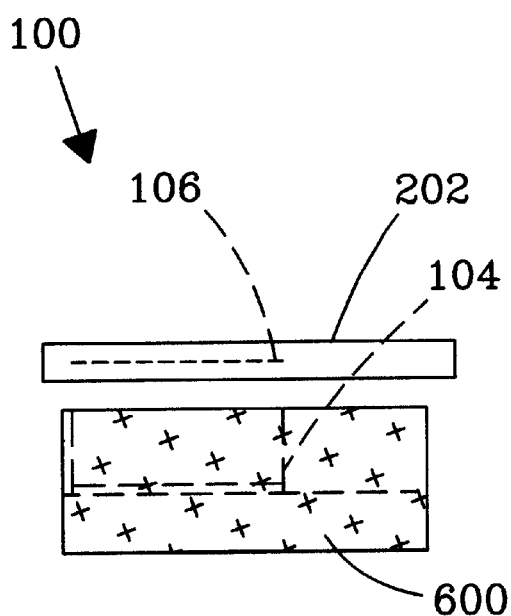
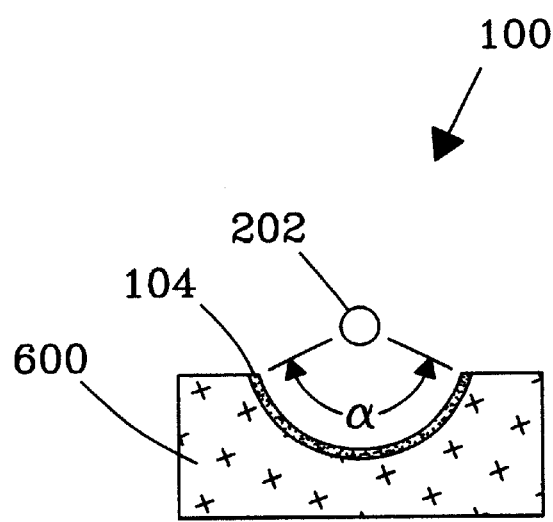
Fig. 7a
Fig. 7b

APPARATUS AND METHOD FOR ULTRASONIC TREATMENT OF A LIQUID

This invention was made with Government support under Contract DE-AC0676RLO1830 awarded by the U.S. Department of Energy. The Government has certain rights in the invention.

FIELD OF THE INVENTION

The present invention is an apparatus and method for ultrasonically treating a liquid-based medium to generate a product. The liquid-based medium, hereinafter referred to simply as "liquid," means single-phase liquids having one or more constituents, as well as liquid-solid mixtures such as suspensions, dispersions, slurries, colloids, and biological tissue.

BACKGROUND OF THE INVENTION

Ultrasound is a form of vibrational energy. When it propagates through, and interacts with, a liquid, the energy is attenuated by scattering or absorption. At low ultrasound powers, the energy is absorbed by the liquid in a thermal interaction that causes local heating. At higher powers the interaction becomes increasingly non-linear and both non-thermal mechanical and cavitational mechanisms become significant. The non-thermal mechanical mechanisms can include radiation pressure, acoustic streaming, radiation forces, torques, and near-boundary/bubble hydrodynamic shear forces.

These ultrasonic interactions with a liquid, particularly those involving cavitation, have been exploited for many years in devices that clean or separate materials, accelerate or modify chemical reactions, and kill or lyse cells. Such devices typically utilize sonic horns, or probes, and are designed to optimize the cavitation mechanism at frequencies generally in the range of 20–50 kHz. For comparison, ultrasound devices used in the medical field typically operate at frequencies of 0.8–15 MHz and at lower power densities (<0.5 W/cm$^2$ for diagnostics and ~0.5–3 W/cm$^2$ for therapy).

Ultrasound offers an attractive cell lysing tool to obtain sufficient amounts of nuclear, cytoplasmic, or other cellular material for commercial use (e.g., proteins), or for analysis and identification (e.g., anthrax or *e-coli*). Effective and rapid lysing is particularly important for the most refractory microorganisms of concern to public health including protozoan cysts, fungal hyphae, Gram positive bacteria, and spores. In a suspension containing microorganisms, the nature of the ultrasound-suspension interaction is complex and has been shown to depend on at least the power level in the ultrasound, the ultrasound field geometry, and frequency of the ultrasound.

Current ultrasound lysing (and other material processing) devices typically use kHz frequencies with a horn or probe configured to optimize cavitation. For a given frequency, there is a minimum power level necessary to cause cavitation, known as the cavitation threshold. In general, the power necessary to achieve cavitation increases with frequency. Thus, when using MHz frequencies, contrast agents (e.g., microbubbles, microparticles) are often introduced in the liquid to help reduce the cavitation threshold by increasing the mechanical interaction and inducing cavitation-like phenomena. In some MHz applications, it is only with the presence of such contrast agents that cavitation occurs.

Because ultrasonic vibration is rapidly attenuated in passing through long paths in a liquid, it is common to effect cell lysis by applying the cavitating kHz ultrasound in a confined chamber. Current sonic lysing devices typically employ a batch processing approach using static liquid reaction chambers. For example, Belgrader et al (Anal. Chemistry, Vol. 71, No. 19, Oct. 1, 1999) employs a horn-based minisonicator for spore lysis and subsequent polymerase chain reaction analysis. Such devices are prone to erosion of the sonic horn tip and unacceptable heating of the liquid.

A few flow-through devices have been developed, though they still incorporate sonic probes depositing energy in a confined chamber. For example, the flow-through devices disclosed in U.S. Pat. No. 3,715,104 and McIntosh and Hobbs (Proc. of Ultrasounics in Industry, pp 6–8, Oct. 20–21, 1970) agitate a liquid between two closely spaced flat surfaces. Furthermore, T. J. Mason (Ultrasonics, 1992, Vol. 30, No. 3, pp 192–196) discloses other flow-through sonic devices that incorporate transducers symmetrically positioned about the flow path of a liquid.

Most current ultrasound processing devices, however, cannot meet the practical, economical, and operational requirements associated with industrial-scale chemical/physical processing systems, field deployable systems, or continuous biomonitoring systems. This is especially true for systems requiring automation or remote operation. Such systems require rapid, effective, efficient, and near-continuous processing with minimal or no manual steps. As the present invention will illustrate, there is an opportunity to apply non-conventional combinations of ultrasonic power, frequency, and field geometry to address current lysing needs and to improve existing (and develop new) chemical and physical processing methods for materials. In particular, ultrasonic treatment at conditions that avoid conventional cavitation and promote non-thermal mechanical interactions shows great potential.

BRIEF SUMMARY OF THE INVENTION

The present invention is an apparatus and method for ultrasonically treating a liquid to generate a product. The apparatus is capable of treating a continuously-flowing, or intermittently-flowing, liquid along a line segment coincident with the flow path of the liquid. The apparatus has one or more ultrasonic transducers positioned asymmetrically about the line segment. The term 'asymmetric' as used herein in relation to asymmetric positioning of transducers means radially asymmetric orthogonal to the axis of the line segment. The ultrasound field encompasses the line segment and the ultrasonic energy may be concentrated along the line segment Lysing treatments have been successfully achieved with efficiencies of greater than 99% using ultrasound at MHz frequencies without the typical cavitation and associated problems, and without the need for chemical or mechanical pretreatment, or contrast agents.

An object of the present invention is to ultrasonically treat a continuously-flowing or an intermittently-flowing liquid to generate a product.

A further object of the present invention is to maximize the amount of product generated for a given transducer power input.

A further object of the present invention is to provide a rapid, effective, and field-deployable ultrasonic treatment system that requires minimal manual intervention.

A further object of the present invention is to lyse cells, producing available nuclear, cytoplasmic, or other cellular material, with greater than 80% efficiency.

A further object of the present invention is to lyse cells in a liquid that does not require chemical or physical pretreatment, or contrast agents.

A further object of the present invention is to improve the productivity of sonochemical and sonophysical treatments that have traditionally been based on batch processing.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWINGS

FIG. 5A is a side view of the full cylinder transducer configuration used in experiment 3;

FIG. 5B is an end view of the full cylinder transducer configuration used in experiment 3;

FIG. 6A is a side view of the piezoelectric element;

FIG. 6B is an end view of the piezoelectric element;

FIG. 7A is a side view of the flow-through device with sonic energy concentrated along a line segment used in lysis experiments 4 and 5; and FIG. 7B is an end view of the flow-through device with sonic energy concentrated along a line segment used in lysis experiments 4 and 5.

DETAILED DESCRIPTION OF THE INVENTION

The present invention is an apparatus and method for ultrasonically treating a liquid to generate a product. The liquid may be a single-phase liquid having one or more constituents (e.g., chemical/petrochemical solutions and biological liquids such as blood plasma and urine) as well as liquid-solid mixtures such as suspensions, dispersions, slurries, colloids, and biological tissue. The liquid-solid mixture may comprise biological material selected from the group consisting of microorganisms, cells, viruses, tissues, and combinations thereof. The product includes, but is not limited to, available nuclear, cytoplasmic, and other cellular material from lysed cells and other materials used in industry that are activated, crystallized, precipitated, sterilized, extracted, impregnated, dispersed, defoamed, degassed, deaggregated, homogenized, or emulsified by the ultrasonic interaction.

The apparatus is capable of treating a continuously-flowing or intermittently-flowing liquid. For example, the process may require a continuously-flowing liquid to optimize the reaction that generates the product, maintain a high operational productivity, or to maintain vigilance in monitoring a biological or chemical threat. Intermittent flows may be implemented in those circumstances where continuous batch treatments are desired.

Figure 1A:
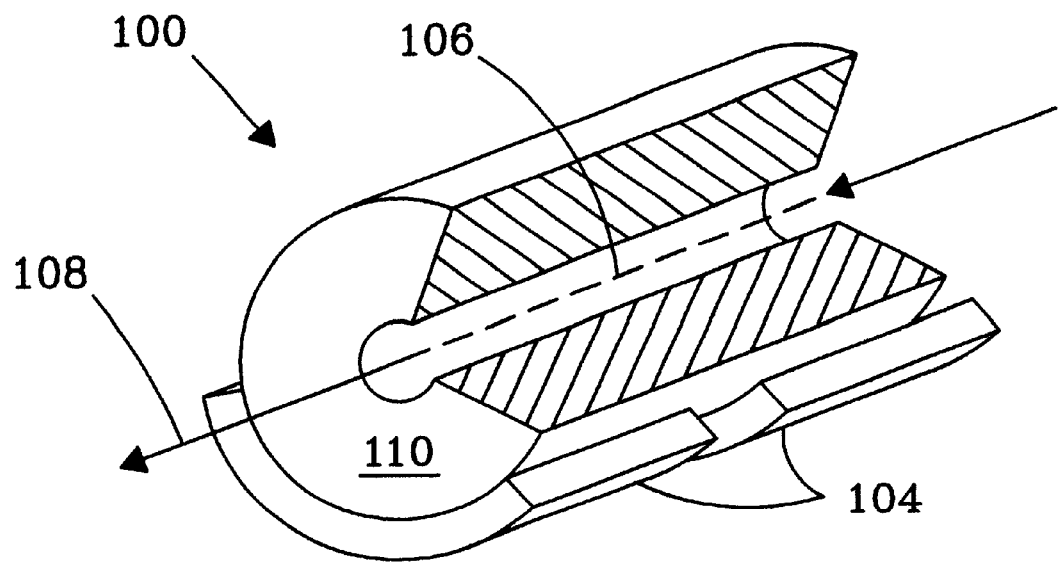
FIG. 1A is an illustration of the present invention with a cylindrical sonic coupler.
Figure 1B:
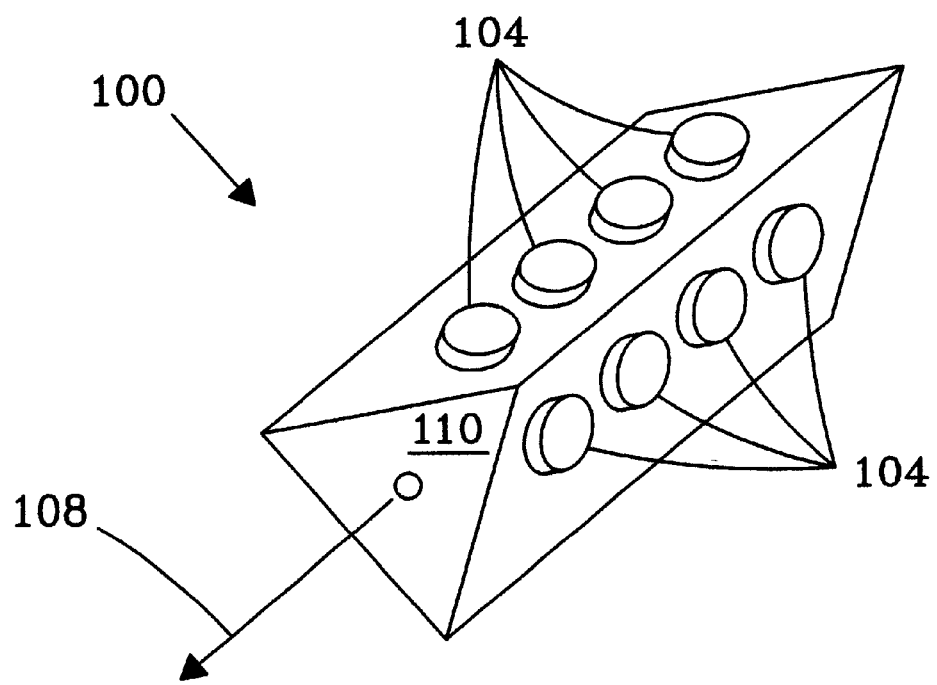
FIG. 1B is an illustration of the present invention with a triangular sonic coupler.
Figure 1C:
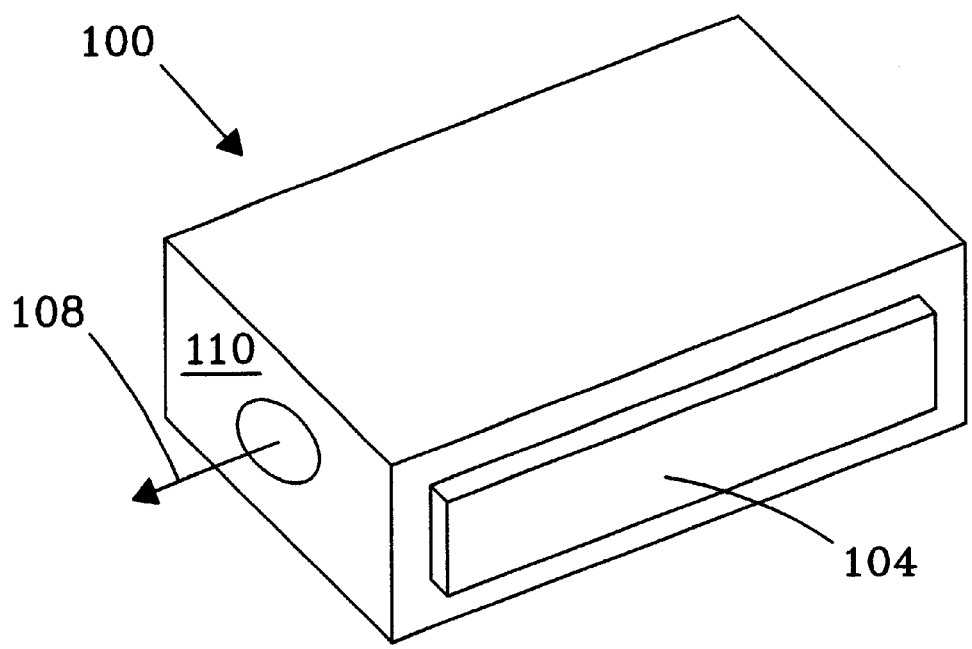
FIG. 1C is an illustration of the present invention with a rectangular sonic coupler.

Several embodiments of the present invention are shown in FIGS. 1A–1C. The liquid to be treated flows along the flow path 108 through the device 100. The liquid in the device 100 is exposed to a unique ultrasound field produced by one or more ultrasound-producing transducer(s) 104 positioned asymmetrically about the flow path 108. The ultrasonic field encompasses the flow path 108 of the liquid within the device 100 including a line segment 106 (see FIG. 1A, not shown in FIGS. 1B–1C for clarity) that is coincident with the longitudinal axis of the flow path 108. The transducer(s) 104 is acoustically coupled to the liquid by a sonic coupler 110. In the embodiments of FIGS. 1A–1B, the transducer(s) are positioned so as to concentrate sonic energy along the line segment 106. The transducer(s) 104 include piezoelectric, magnetorestrictive, and other devices capable of producing an ultrasonic field. The line segment 106 may be straight or curved. For example, the line segment 106 (and flow path 108) may be helical to increase the residence time (and thus, treatment time) of the liquid in the sonic field.

In these embodiments, the sonic coupler 110 is a solid material that may be rigid or flexible, and provides the flow path 108 for the liquid (the liquid may enter and exit the device 100 along the flow path 108 by connecting tubing or piping (not shown) to the entrance and exit of the device 100). It is preferable that the sonic coupler 110 is made of a material with a low attenuation coefficient to avoid overheating of the sonic coupler 110 and has an acoustical impedance value between the acoustical impedance of the liquid and that of the transducer(s) 104. For example, aqueous liquids have an acoustical impedance of approximately $1.5 \times 10^6$ kg/m$^2$/s and piezoelectric transducer materials (e.g., high density ceramics) typically have acoustical impedances in the range of $20 \times 10^6$–$36 \times 10^6$ kg/m$^2$/s. Thus, candidate sonic coupler 110 materials include metals (e.g., aluminum), ceramics, glasses, minerals, and combinations thereof. Due to the various geometries that may be required to obtain an asymmetric positioning of the transducer(s) 104, it is preferable that the sonic coupler 110 is easily machinable such as a machinable ceramic. Machinable ceramics include glass-mica (e.g., MACOR®, MACOR is a registered trademark of Corning Glass Works), boron-nitrate, aluminum silicate, alumina bisque, and combinations thereof.

It is more preferable that the sonic coupler 110 is made of a material with an acoustical impedance value approximately equal to the geometric mean of the acoustical impedances of the liquid and the transducer(s) 104. For example, if the liquid and transducer(s) 104 have acoustical impedances of $1.5 \times 10^6$ kg/m$^2$/s and $30 \times 10^6$ kg/m$^2$/s, respectively, a material having an acoustical impedance of $(1.5 \times 30)^{1/2}$= 6.7 would be more preferred.

As known to those skilled in the art, there are various methods to ensure an adequate acoustical coupling between the transducer(s) 104 and the sonic coupler 110 itself. For example, the two components may be epoxied together or machined to a close fit and smooth surface finish that minimizes loss of ultrasound energy associated with gaps between the two components.

Though the embodiments of the present invention shown in FIGS. 1A–1C illustrate cylindrical, triangular, and rectangular sonic couplers 110 and various numbers of cylindrical and planar transducer(s) 104, the present invention is not limited to such shapes and numbers. For example, the sonic coupler 110 may be hexagonal (or oval) with one or more planar transducer(s) 104 asymmetrically positioned on the sonic coupler 110. In addition, the transducer(s) 104 may comprise a single transducer and be concave with the sonic coupler 110 machined or shaped to accommodate such transducer(s) 104 geometry.

Figure 2:
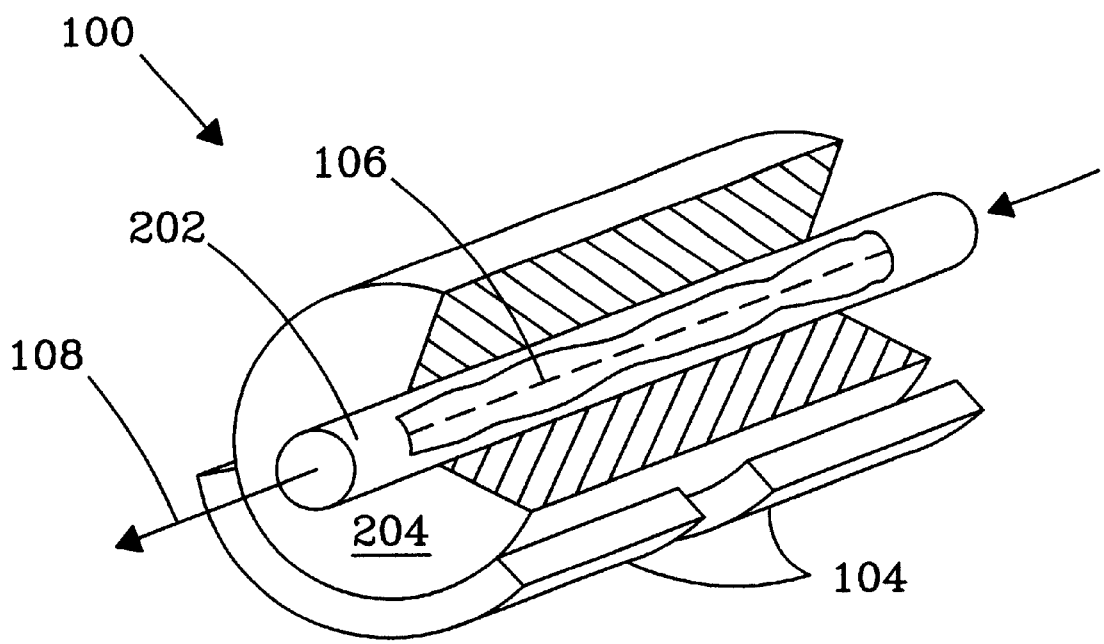
FIG. 2 is an illustration of the present invention with a reaction tube.
Figure 3:
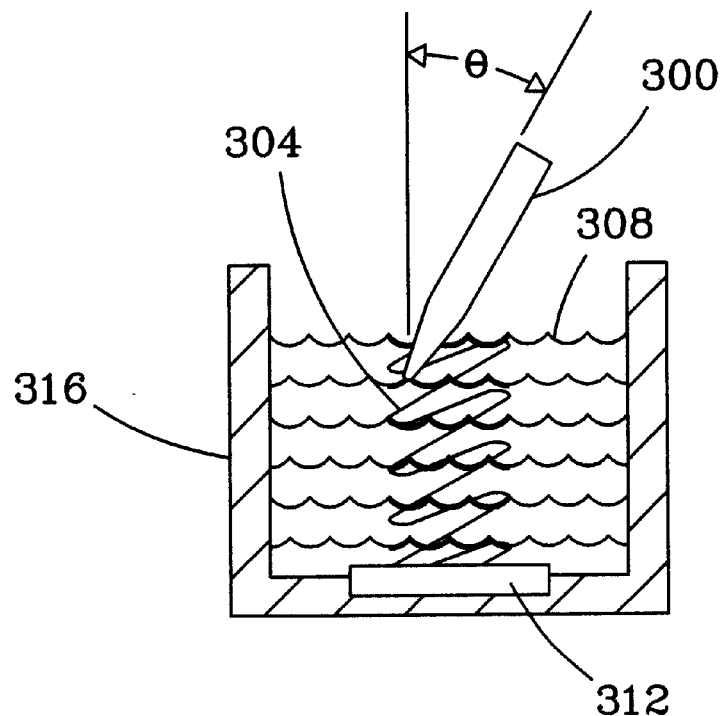
FIG. 3 is an illustration of a static liquid chamber used in lysis experiment 1.

An alternative embodiment of the present invention is the device 100 shown in FIG. 2. In this embodiment, the sonic coupler 110 of FIGS. 1A–1C is replaced by a reaction tube 202 and a reaction tube coupler 204. The reaction tube 202 provides the flow path 108 for the liquid and is acoustically coupled to both the liquid and the reaction tube coupler 204. As in the previous embodiments, the reaction tube coupler 204 is acoustically coupled to the transducer(s) 104. The reaction tube 202 may be made of any structural material that is compatible (e.g., chemically) with the fluid and reaction tube coupler 204 including, but not limited to, metal, glass, and plastic. In this embodiment, the reaction tube coupler 204 can be made of the same material (and in the same shape) as the sonic coupler 110 of the embodiments shown in FIGS. 1A–1C or it can be a liquid, preferably water. Though the reaction tube coupler 204 is illustrated as being cylindrical in FIG. 2, the present invention is not limited to such a shape, especially if the reaction tube coupler 204 is a liquid. In such circumstances, a requirement is that the liquid provide sufficient acoustical coupling between the reaction tube 202 and the reaction tube coupler 204 (for example, by immersing the reaction tube 202 and the reaction tube coupler 204 in a liquid bath).

Furthermore, though the embodiments of the present invention shown in FIGS. 1A–1C and FIG. 2 illustrate a single flow path 108, the present invention is not limited to a single flow path 108. That is, it is apparent that multiple flow paths could be incorporated in the device 100 of FIGS. 1A–1C and FIG. 2 (e.g., to increase the volumetric processing or treatment rate of the liquid).

The following successful experiments, with the notable exception of experiment 3, illustrate new combinations of ultrasound power, frequency, and field geometry that meet the challenge of lysing *Bacillus globigii* (BG) spore suspensions. Such successful lysis experiments are not intended to limit the present invention to such a specific biological treatment. It will be apparent to those skilled in the art that the present invention overcomes drawbacks of current ultrasonic treatments beyond lysing and opens up new sonochemical and sonophysical treatments for material processing industries including, but not limited to, chemical, biochemical, petrochemical, food, and mining.

Furthermore, though some details on how the fluid in the present invention is made to flow through the device 100 are provided below, such features should not be interpreted as limitations to the present invention. That is, there are many different mechanisms to cause the liquid to flow (pumps, pneumatic, gravity feed, etc.) and a variety of piping and valving arrangements to have the liquid flow intermittently. The variety of components and arrangements to accomplish fluid flow in the present invention are known to those skilled in the art of fluid systems.

Experimental Procedure

BG spore suspensions originated from stock preparations maintained at Dugway Proving Grounds. Spores were resuspended in sterile water and subjected to several rounds of vigorous mixing, settling and decanting to eliminate spore clumps. Plate counts and microscopy were used to confirm the consistency of the stock spore suspension and verify that a single spore gave rise to a single colony. A suspension of $10^8$ spores/ml was used for all lysis experiments described below.

Ten-fold serial dilutions of spore suspension were prepared in sterile water within two hours of all lysis experiments. Three×20 $\mu$l aliquots were spotted directly onto trypticase soy agar (Difco, Detroit, Mich.) plates and incubated at 30° C. for 36 hours. All lysis and plating experiments were performed in triplicate, resulting in at least 9 data points (spore counts) for each treatment. Lysis efficiency was calculated as $100\times(C_o-C_{lysis})/C_o$; where $C_o$ is the viable spore count before lysis and $C_{lysis}$ is the viable spore count after lysis.

The original spore preparation had significant quantities of adsorbed deoxyribonucleic acid (DNA) on the spore coat that interfered with polymerase chain reaction (PCR) detection of intracellular or liberated BG DNA. Eight hundred microliter aliquots of BG spores were collected by centrifugation and resuspended in 200 $\mu$l 10% sodium hypochlorite for 1–10 minutes. After this decontamination, spores were recovered by centrifugation, washed extensively in sterile water, and then subjected to on-line lysis (described in the experiments below) and PCR amplification. Control lysis experiments showed that the hypochlorite treatment had no effect on cell lysis efficiency, spore viability, or carryover of PCR inhibitors.

DNA availability after spore lysis was assessed by a dilution-to-extinction PCR method. Genomic DNA was isolated from BG spores by bead-mill homogenization and quantified by ultraviolet spectrophotometry. PCR primers Bg215f and Bg325r were provided by Navy Medical Research Institute and synthesized by Keystone Labs (Camarillo, Calif.). PCR amplification was carried out in 25 $\mu$l total volume, utilizing an M J Research (Watertown, Mass.) Tetrad thermal cycler and 0.2 ml thin-walled reaction tubes. Spore preparations (lysed or unlysed) were serial diluted in a 10-fold series immediately prior to PCR, and purified BG DNA was serially diluted in PCR-grade water at 100 pg to 1 fg $\mu$l-1 as a positive control template. Final reaction conditions were 5 $\mu$l DNA or lysed/unlysed spore preparation, 10 mM Tris pH 8.3, 50 mM KCl, 2.5 mM MgCl2, 200 $\mu$M each dNTP, 0.2 $\mu$M each primer, 5 $\mu$l template DNA or lysed spore suspension, and 0.625 U LD-Taq polymerase (Perkin Elmer, Foster City, Calif.) which had been pretreated with TaqStart™ antibody at the recommended concentration (Sigma, St. Louis, Mo.). Assembled reactions were amplified with 45 cycles at 94° C. for 15 s, 56° C. for 30 s, 72° C. for 30 sec with a 2 s extension per cycle. The entire contents of each PCR were analyzed on 1% NuSieve, 1% Seakem GTG agarose (FMC Bioproducts, Rockland, Me.) gels in 1×TAE running buffer, both containing ethidium bromide, and gel images captured with a BioRad (Hercules, Calif.) Fluor-S imager and Molecular Analyst software.

Experiment 1

Experiment 1 demonstrated that cell lysis can be performed with greater than 99% efficiency using 1 MHz ultrasound both with and without the addition of contrast agents. FIG. 3 shows an initial static-liquid chamber lysis experiment using 1 MHz ultrasound, whereby the bottom of a standard polypropylene microfuge tube 300, containing a 200 microliter suspension of BG, was held in place in a water bath 308 in the sonic field 304 produced by the transducer 312 in an ultrasonic humidifier 316. The angle of the microfuge tube, θ, was set to zero (i.e., the tube was vertical) for this particular experiment. The specific humidifier 316 was a Holmes Ultrasonic humidifier, model HM-460B, ca. 10 W/cm$^2$ peak power. Sixty milligrams of 50 micron glass microspheres and 40 micrograms of paramagnetic particles were added (in separate subexperiments) to help induce cavitation and/or enhance collision rates.

Though this experiment did not utilize a flowing liquid, the results, shown in Table 1 below, clearly indicate that cell lysis can be obtained in a MHz sonic field. The presence or absence of microparticles had no appreciable effect on spore lysis efficiency or in-tube temperature, suggesting that the added microparticles were neither acting as an energy sink nor microbubble source during the course of the experiment. This system also caused up to a 5-log reduction in cell viability for vegetative *Escherichia coli, Bacillus aetrophaeus* and *Bacillus thuringiensis* kurstaki cells, with extensive cellular damage as determined by light microscopy. All subsequent experiments were therefore performed without microparticles, as would be advantageous in an automated biomonitoring system.

TABLE 1

Percent lysis efficiency of BG spores in a static liquid vertical chamber using MHz ultrasound.

| 4 × 30 sec with: | % Lysis Efficiency | In-Tube Average Temp. (° C.) |
| --- | --- | --- |
| No Beads | 99.4 | 104 |
| Glass Beads | 99.6 | 104 |
| Magnetic Beads | 99.1 | 103 |

Experiment 2

Figure 4:
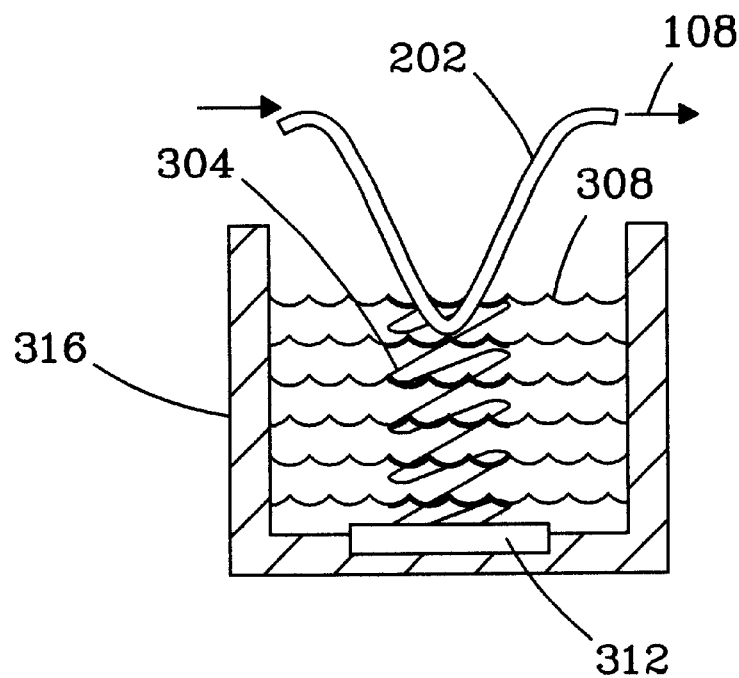
FIG. 4 is an illustration of a flow through chamber used in lysis experiment 2.

The first "flow-through" sonic device experiment is illustrated in FIG. 4, whereby the same humidifier 316, transducer 312, and water bath 308 as that of experiment 1 was used. In experiment 2, however, a reaction tube 202 made of 3.2 mm OD×1.5 mm ID TEFLON® (i.e., polytetrafluoroethylene, TEFLON is a registered trademark of E. I. Dupont de Nemours and Company) and one made of 3.2 mm OD×1.5 mm ID polyetherethylketone (PEEK) chromatography tubing were used in two separate subexperiments. Note that in this experiment, the water bath 308 functions as the reaction tube coupler 204 of FIG. 2. The reaction tube 202 was connected to a standard sequential injection system (FiaLab 3000, Alitea, USA) that included a 1 ml syringe pump (Cavro, Sunnyvale, Calif.) and a 10-port selection valve (Valco, Cheminert, Houston, Tex.). The flow injection system delivered a continuous flow (at 1 $\mu$l/s and 5 $\mu$l/s) of BG spore suspension through the reaction tube 202 that was partially immersed in the 1 MHz sonic field 304 produced by the transducer 312. As shown in FIG. 4, the sonic field 304 encompassed a line segment 106 (not shown for clarity) coincident with the flow path 108 in the trough region of the reaction tube 202. The line segment 106 was approximately 5 mm in length, resulting in 0.5 to 2.5 second exposure of spores to the sonic field as opposed to the 1 to 2 minutes of exposure employed in the previous batch experiment 1. Also introduced were 15 $\mu$l air segments every 10 $\mu$l of spore suspension to mimic the air/liquid interface present in experiment 1. In all cases, the total volume of spore suspension processed was 200 $\mu$l.

Results from this experiment are shown in Table 3 below, which demonstrate that a MHz sonic field can effect spore lysis in a near-instantaneous manner. Air segmentation appeared to significantly enhance lysis efficiency in the TEFLON tubing, but this interaction was not pursued because TEFLON tubing melted during the course of the trials (40–200 seconds continuous power). PEEK tubing, on the other hand, withstood the sonic energy and maintained in-tube temperatures near 100° C., but air segmentation had little effect on lysis efficiency. Control plating experiments (no lysis) showed that BG spores were not retained within the fluidics system, such that all plate counts associated with Table 3 reflect treatment effects on BG spores rather than cross-contamination and carryover between lysis trials. All further experiments were conducted in PEEK tubing in the absence of any air segmentation or microbubble amendments, again compatible with a field deployable and automated biomonitoring system.

TABLE 3

Percent lysis efficiency of BG spores in a flow-through MHz lysis experiment.

|  | No Air | Plus Air |
| --- | --- | --- |
| TEFLON TUBING | | |
| 1 $\mu$l sec$^{-1}$ | 82.4 | 99.3 |
| 5 $\mu$l sec$^{-1}$ | 21.2 | 72.0 |
| PEEK TUBING | | |
| 1 $\mu$l sec$^{-1}$ | 90.4 | 88.9 |

Experiment 3

The previous two experiments show that the liquid residence time in the sonic field is an important variable for effective cell lysis. Consequently, a device wherein the sonic energy is concentrated along a line segment 106 throughout the entire length of the transducer(s) 104 was developed as shown in FIGS. 5A–5B.

The transducer(s) 104 was a commercial 1.48 MHz cylindrical piezoelectric element shown in FIGS. 6A–6B and placed in high density foam 600 to absorb the energy radiating outward from the diameter of the transducer(s) 104. A Hewlett Packard 33120A 15 MHz function/arbitrary waveform generator was used and frequency was monitored with an ENI A-300 RF power amplifier and Tektronix TDS 460-A 4 channel digitizing oscilloscope. It was presumed that such a symmetrical configuration would provide a high-intensity field along the line segment 106 (i.e., along the longitudinal axis of the transducer(s) 104) for subsequent processing of a fluid flowing along the line segment 106.

The entire configuration was immersed in water. When power was applied to the transducer(s) 104, only a small amount of acoustic activity was observed near the ends of the transducer(s) 104. While ultrasonic pressure may have been developed along the line segment 106, no acoustic streaming was observed and it did not appear to provide sufficient sonic energy desired for lysis. This is understandable based on the effect of acoustic wave cancellation caused by the symmetry of the device.

Experiment 4

Whereas the previous experiment demonstrated unsatisfactory sonic energy with a symmetrical configuration, an asymmetric configuration (shown in FIGS. 7A–7B) was demonstrated to provide sufficient energy. In this embodiment, the device 100 used a transducer(s) 104 in the form of a partial cylinder representing less than half the full cylinder used in experiment 3. Based on the results of experiment 3, if the cross-sectional arc α is greater than 180°, the sonic field generated would oppose itself at the opposite side of the cylinder and decrease the field intensity along the longitudinal axis of the transducer(s) 104. Therefore, the transducer(s) 104 was fabricated from a section of the commercial 1.48 MHz cylindrical piezoelectric element (FIGS. 6A–6B) with a cross-sectional arc, α, equal to 160° (FIGS. 7A–7B). The transducer(s) 104 was placed in high density foam 600 to absorb the energy radiating outward from the diameter of the transducer(s) 104. This asymmetric geometry was used to concentrate sonic energy along the line segment 106 coinciding with the longitudinal axis of the reaction tube 202. The reaction tube 202, made of 3.2 mm OD×1.5 mm ID PEEK tubing, was positioned approximately at the central axis of the transducer(s) 104. In such a configuration, liquid residence time and temperatures in the reaction tube 202 are a function of flow rate, and incident sonic energy a function of power, frequency, and distance from the transducer(s) 104. Temperatures in the reaction tube 202 were recorded with a thermocouple (not shown). Acoustic power intensity was measured at various points in the sonic field with a calibrated pin transducer (not shown).

The entire configuration was immersed in water (serving as the reaction tube coupler 204, not shown) to acoustically couple the transducer(s) 104 to the reaction tube 202. Under the proper driving power, this configuration gave excellent lysis results. Two hundred microliter aliquots of spore suspension were flowed through the reaction tube 202 at 1 $\mu$l sec$^{-1}$ at variable power (700, 800, 900 and 1000 mV) and at variable distances between the reaction tube 202 and transducer(s) 104. Lysis efficiencies of greater than 99% were obtained with this device, with sample temperatures staying at or below 106° C. as shown in Table 4 below.

TABLE 4

Percent lysis efficiency and sample temperature as function of power input.

| Distance | Power (mV) | % Lysis | In-tube Temp. (° C.) |
|---|---|---|---|
| 15 mm | 700 | 99.7 | 78–101 |
|  | 800 | 99.9 | 100–101 |
|  | 900 | 99.8 | 100–101 |
|  | 1000 | 99.2 | 100–102 |
| 20 mm | 700 | 99.6 | 95–103 |
|  | 800 | 99.3 | 95–104 |
|  | 900 | 97.7 | 101–106 |
|  | 1000 | 97.6 | 101–105 |
| 26 mm | 700 | 88.3 | 45–72 |
|  | 800 | 97.8 | 80–92 |
|  | 900 | 99.7 | 95–101 |
|  | 1000 | 99.9 | 99–101 |

The sonic field was highly concentrated along the line segment 106 of the device 100 except at the ends where the edge effect of the transducer(s) 104 gave a typical high peak. Measurement of acoustic emissions with a pin transducer failed to show characteristic cavitation noise, supporting a non-cavitation, non-thermal mechanical lysing mechanism. Since there is no correlation between in-tube temperature and lysis efficiency, these results suggest that a continuous-flow, low-temperature, high-efficiency lysis system can indeed be constructed with judicious selection of transducer(s) 104 and physical geometry.

Experiment 5

An experiment was also conducted to compare lysis efficiency obtained using degassed and standard liquid solutions. The device 100 of experiment 4 was used and the spore solution was passed through the reaction tube 202 positioned 15 mm above the transducer(s) 104. 200 $\mu$l of the spore solution was processed at a flow rate of 1 $\mu$l/s. The data, shown in Table 5, shows that greater than 98% lysis efficiency was achieved for both standard and degassed solutions exposed to two different sonic field intensities. Since the removal of bubbles in the degassed solution did not significantly decrease the lysis efficiency, this result further supported the hypothesis that cavitation is not the primary mechanism of spore lysis in the device 100.

TABLE 5

Percent spore lysis efficiency obtained in degassed and standard solutions.

| Degassed | Power (mV) | % Lysis |
|---|---|---|
| yes | 700 | 98.6 |
| no | 700 | 99.2 |
| yes | 800 | 99.3 |
| no | 800 | 99.6 |

Closure

While embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method for ultrasonically treating a liquid in a flow path, comprising the steps of:
   a. positioning at least two ultrasound-producing transducers asymmetrically about a line segment, said at least two transducers producing a concentrated sonic field encompassing said line segment;
   b. providing said flow path for the liquid coincident with said line segment;
   c. acoustically coupling said at least two transducers to the liquid in said flow path;
   d. energizing said at least two transducers with a power supply; and
   e. operating said at least two transducers at a frequency wherein ultrasonic treatment of a liquid is from non-thermal and non-cavitating ultrasonic interactions.

2. The method of claim 1, wherein said at least two transducers concentrate sonic energy along said line segment.

3. The method of claim 1, wherein the liquid is flowing continuously in said flow path.

4. The method of claim 1, wherein the liquid is flowing intermittently in said flow path.

5. The method of claim 1, wherein the liquid is a single-phase liquid.

6. The method of claim 5, wherein said single-phase liquid is biological.

7. The method of claim 1, wherein the liquid is a liquid-solid biological material mixture selected from the group consisting of suspension, dispersion, slurry, colloid, and biological tissue.

8. The method of claim 1, wherein the liquid is a liquid-solid mixture comprising biological material selected from the group consisting of microorganisms, cells, viruses, tissues, and combinations thereof.

9. The method of claim 1, wherein the liquid comprises a petrochemical.

10. The method of claim 1, wherein said treating the liquid is lysing biological material in the liquid.

11. The method of claim 1, wherein said treating the liquid is a chemical process selected from the group consisting of activating, crystallizing, precipitating, and combinations thereof.

12. The method of claim 1, wherein said treating the liquid is a physical process selected from the group consisting of sterilizing, extracting, impregnating, dispersing, defoaming, degassing, deaggregating, homogenizing, emulsifying, and combinations thereof.

13. The method of claim 1, wherein said at least two transducers operate at a frequency in the range from 0.5 to 5 MHz.

14. A method for ultrasonically treating a liquid in a flow path, comprising the steps of:
   a. positioning at least two ultrasound-producing transducers asymmetrically about a line segment, said at least two transducers producing a concentrated sonic field encompassing said line segment;
   b. providing said flow path for the liquid coincident with said line segment;
   c. acoustically coupling said at least two transducers to the liquid in said flow path;
   d. energizing said at least two transducers with a power supply; and
   e. operating said at least two transducers at a frequency wherein cavitation cannot be detected and ultrasonic treatment of a liquid results essentially from non-thermal mechanical mechanisms.

15. A method for ultrasonically treating a liquid in a flow path, comprising the steps of:
   a. positioning at least two ultrasound-producing transducers asymmetrically about a line segment, said at least two transducers producing a concentrated sonic field encompassing said line segment;
   b. providing said flow path for the liquid coincident with said line segment;
   c. acoustically coupling said at least two transducers to the liquid in said flow path;
   d. energizing said at least two transducers with a power supply;,and
   e. operating said at least two transducers at a frequency wherein cavitation does not occur and ultrasonic treatment of a liquid results essentially from non-thermal mechanical mechanisms.

* * * * *